United States Patent [19]

Gorisch

[11] Patent Number: 4,812,613
[45] Date of Patent: Mar. 14, 1989

[54] BEAM GUIDING OPTICAL SYSTEM FOR LASER RADIATION

[75] Inventor: Wolfram Gorisch, Aschaffenburg, Fed. Rep. of Germany

[73] Assignee: W. C. Heraeus GmbH, Hanau, Fed. Rep. of Germany

[21] Appl. No.: 143,965

[22] Filed: Jan. 13, 1988

[30] Foreign Application Priority Data

Mar. 21, 1987 [DE] Fed. Rep. of Germany ....... 3709351

[51] Int. Cl.$^4$ ............................................. B23K 26/06
[52] U.S. Cl. .............................. 219/121.74; 128/303.1; 350/620
[58] Field of Search ....................... 219/121.74, 121.67, 219/121.72, 121.68, 121.69; 350/619, 620, 622; 128/303.1

[56] References Cited

U.S. PATENT DOCUMENTS 3,986,767 10/1976 Rexer et al. ................ 215/121.74 X
4,192,573 3/1980 Brown, Jr. ...................... 350/619 X Primary Examiner—C. L. Albritton
Attorney, Agent, or Firm—Felfe & Lynch

[57] ABSTRACT

A beam guiding optical system for laser radiation, especially for the radiation of a medical laser, for the continuous adjustment of focal length is described, which is distinguished by the fact that aberrations are largely prevented. The beam guiding optical system preferably has a linearly movable carriage with at least two carriage mirrors disposed fixedly with respect to one another, at least one of these carriage mirrors being concavely or convexly curved, and the beam axis of the entry beam falling on a mirror being parallel to the beam axis of the beam emerging from the adjusting means. The axis of displacement of the carriage is aligned parallel to the beam axis of the entry and emerging beam. In the beam path outside of the adjusting means there is disposed at least one deflecting mirror which has a curvature complementary to the curvature of the at least one curved carriage mirror. These mirrors are surface elements of solids of rotation of cone sections, which are aligned with one another such that the corresponding focal points of the at least one deflecting mirror in the beam path outside of the adjusting means lie in the plane which is spanned by the incident and reflected beam of the aforesaid at least one deflecting mirror.

11 Claims, 5 Drawing Sheets

BEAM GUIDING OPTICAL SYSTEM FOR LASER RADIATION

The invention relates to a beam guiding optical system for laser radiation, especially for the radiation of a medical laser, for the continuous adjustment of the focal length, having at least one concave reflector and adjusting means acting on parts of the beam guiding optical system.

A beam guiding optical system for surgical purposes is disclosed in U.S. Pat. No. 4,396,285. The laser system therein described, which has a working laser and an aiming laser, has a pivoting, concavely curved mirror whereby the position of the focal point of the laser beam in the working plane can be varied. This arrangement does not provide the possibility of varying the focal length and with it the position of the focal point.

Also known are lens systems for laser systems, which usually have a helium-neon aiming laser and a $CO_2$ working laser; in these lasers the focal length can be variably adjusted by displacing the lenses. Such optical systems, which contain lenses, have dispersion, so that, as a result of the different wavelengths of the aiming laser and working laser, the focal points of the aiming laser and working laser do not coincide in their position in space. If beams strike the center of the lenses, the focal points diverge longitudinally. If they strike them off-center, they also diverge laterally; thus the aiming beam fails its purpose.

It is an object of the present invention, therefore, to provide a new and improved beam guiding optical system for laser radiation which avoids one or more of the disadvantages of such prior systems.

It is another object of the present invention to provide a new and improved beam guiding optical system, especially for the radiation of a medical laser, in which the focal length is continuously variable, and any aberration, e.g., due to the dispersion of optical lens imaging systems, is largely avoided.

These objects are achieved by the fact that the adjusting means comprises a linearly movable carriage which carries at least two carriage mirrors disposed with respect to one another, at least one of these carriage mirrors being concavely or convexly curved; that the beam axis of the input beam falling on the one mirror is parallel to the beam axis of the beam issuing from the adjusting means, the axis of displacement of the carriage being parallel to the beam axis of the input and output beam; that at least one deflecting mirror is disposed in the beam path outside of the adjusting means, which has a carriage mirror of a curvature complementary to the curvature of the aforesaid at least one curved carriage mirror, the mirrors of complementary curvature, which are surface elements composed of solids of revolution of conic sections, being aligned with one another such that the corresponding focal points of the particular mirror lie in the plane which is spanned by the incident and reflected beam of the particular mirror.

It is important that the laser beams be reflected both by a concave and by a convex mirror before they fall upon the working field. The mirrors disposed for adjustment of the distance between them permit shifting the focal point in the direction of the beam. Aberrations due to dispersion are largely prevented by the two mirrors of complementary curvature disposed in the beam path, since no optical refraction occurs, as would be the case with optical lenses. The use of mirrors of complementary curvature, which are surfaces of solids of revolution of conic, sections, i.e., ellipsoids or paraboloids which have anisotropic radii of curvature in at least one of the two directions perpendicular to one another, prevent aberrations. The geometrical shape of the ellipsoids and paraboloids can be computed by means of the known mathematical formulas for the determination of conic sections, the necessary focal lengths being able to be given by the geometric optical or Gaussian optical course of the beam.

If slight aberrations are to be tolerated, then toroidal mirrors can be used instead of the solids of revolution of conic sections. For example, the radii of curvature of such toroidal mirrors are to be selected as $R/k$ and, in the direction perpendicular thereto, as $R \times k$, wherein $k = \sqrt{2}$ (for an angle of incidence of 45°). By arranging the mirrors within the carriage such that the beam axes of the beam entering and leaving the adjusting means are parallel to one another and the carriage is to be shifted parallel to the beam axes, i.e., in the direction of the beam axes, it is possible in a simple manner to adjust the focal length of the optical system and with it the position of the focal point.

The concavely or convexly curved mirror is used preferably as the carriage mirror on the exit side, with regard to the beam direction. A planar mirror can be used as the entry side carriage mirror within the adjusting means or carriage.

Depending on the desired location of the focal point and on the required beam diameter, the carriage mirror on the entry side can be in the form of a convex or concave mirror, in which case the at least one deflecting mirror provided in the beam path outside of the adjusting means, which reflects the beam toward the working plane, has a curvature corresponding to the carriage mirror on the entry side.

Preferably the deflecting mirror is disposed for pivoting about at least one axis perpendicular to the beam axis, so that, in addition to the focal point adjustment, the system permits the focal point to swing in a particular working plane. This permits the focal point of the laser radiation to be adjustable in two additional directions in space, i.e., a total of three.

The adjusting means and the deflecting mirror can be made in a single unit, which is then preferably disposed on a beam guiding arm having a plurality of articulations, so that the focal point can be moved about by such a beam guiding optical system in a variety of working planes variously oriented in space.

In a constructively simple embodiment, the carriage is displaced linearly by means of a gear drive, preferably such that the carriage is guided in a groove and bears a rack which is displaced together with the carriage by a pinion meshing therewith. Other displacement mechanisms are possible, especially in the form of a cylinder and piston.

In accordance with the invention, a beam guiding optical system for laser radiation, especially for the radiation of a medical laser, for the stepless variation of the focal length comprises adjusting means acting on parts of the beam guiding optical system. The adjusting means comprises a linearly movable carriage which bears at least two carriage mirrors disposed with respect to one another. At least one of these carriage mirrors is concavely or convexly curved. An entry beam falls on a mirror having a beam axis which is parallel to a beam axis of a beam emerging from the adjusting means. The carriage has an axis of displacement which is aligned parallel to the beam axis of the entry and emerging beams. At least one deflecting mirror is disposed in a beam path outside of the adjusting means, which has a carriage mirror of a curvature complementary to the curvature of the aforesaid at least one curved carriage mirror. The mirrors of complementary curvature, which are surface elements of solids of rotation of conic sections, are aligned with one another such that the corresponding focal points of the at least one deflecting mirror in the beam path outside the adjusting means lie in the plane which is spanned by the incident and reflected beam of the aforesaid at least one deflecting mirror.

For a better understanding of the invention, together with other and further objects thereof, reference is made to the following description, taken in connection with the accompanying drawings, and its scope will be pointed out in the appended claims.

Referring now to the drawings.

Figure 1:
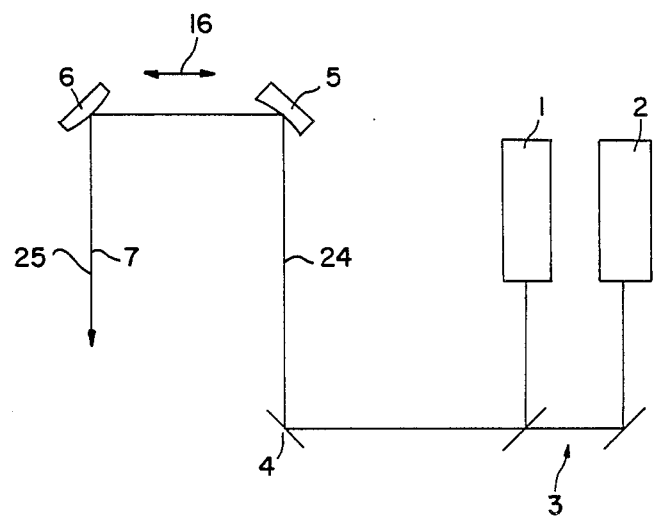
FIG. 1 shows diagrammatically a laser system with a beam guiding optical system according to the invention.

Referring now more particularly to FIG. 1, the laser system shown in FIG. 1 has a neon laser as its pilot or aiming laser 1, and as its working laser 2 a carbon dioxide laser; their beams are brought together before they fall upon a deflecting mirror 4. From this deflecting mirror 4 the beams strike a concave mirror 5 and a convex mirror 6 in the direction of the working plane as indicated by the arrow 7.

Figure 2:
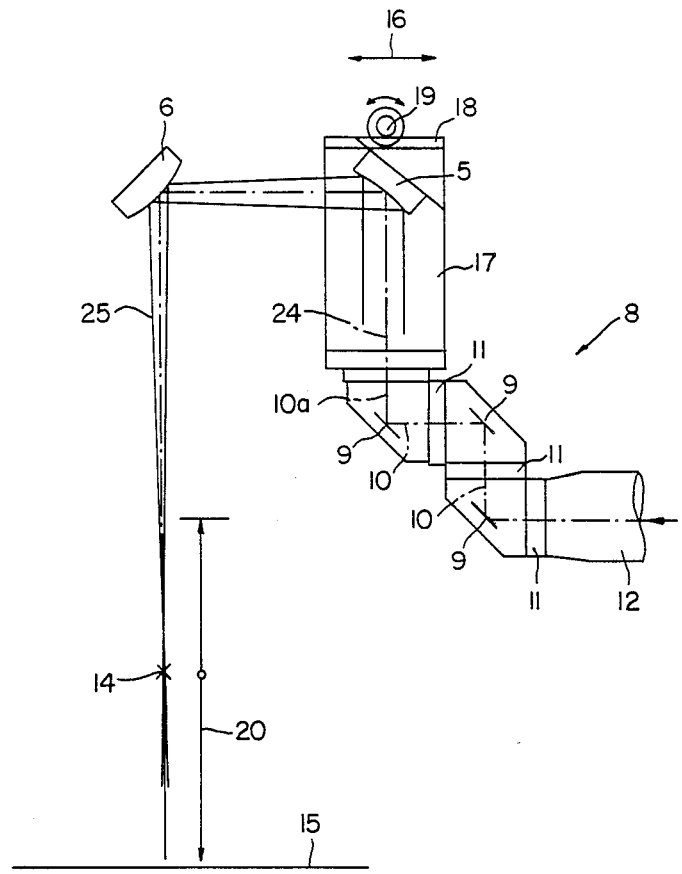
FIG. 2 is a detailed diagrammatic representation of the beam guiding optical system of FIG. 1.

As FIG. 2 shows, the concave mirror 5, as it is indicated in FIG. 1, is disposed at the end of a beam guiding arm 8. This beam guiding arm 8, which is an articulated mirror arm, has three planar mirrors 9, each in a link 10, which deflect the beam each by 45°. The individual links 10 are joined together by two joints 11; an additional joint 11 is disposed between the first joint 11, as seen in the direction of the beam, and an arm 12. By means of the three joints 11, and in some cases by an additional joint (not shown) at the end of the last line 10a, the concave mirror 5 and the deflecting mirror 6 can be turned in any desired direction in space, and from this it follows that the deflecting mirror 6 is also carried by the beam guiding arm.

The parallel laser beams are focused on a common focal point 14 by the two mirrors 5 and 6, the deflecting mirror 6 being a convex mirror in the embodiment according to FIG. 2. To vary the position of the focal point 14 perpendicular to the working plate 15, the distance between the convex deflecting mirror 6 and the concave mirror 5 is varied. For this purpose the beam guiding arm 8 preferably is made displaceable horizontally in the direction of the arrow 16, in guides which are not shown in detail. To be able to adjust continuously the distance between the two mirrors, preferably a pinion 19 engages a rack 18 which is fastened to the upper end of the carriage 17. This drive can also, for example, be in the form of a worm gear drive.

In the embodiment according to FIG. 2, the distance between the convex deflecting mirror 6 and the concave deflecting mirror 5 is varied for the adjustment of the focal point 14 (the range of adjustment of the focal point is indicated by the arrows 20) by varying the beam guiding arm 8 with the concave mirror 5 disposed therein, relative to the deflecting mirror 6. In the embodiment according to FIG. 3, however, both the deflecting mirror 6 and the beam guiding arm 8' are fixed in their distance one from the other, but the carriage 17 is displaced between the deflecting mirror 6 and the beam guiding arm 8' by means of the rack-and-pinion drive 18 and 19. Within the carriage 17, in contrast to the embodiment in FIG. 2, an additional planar mirror 21 is disposed, which reflects the beam from the last planar mirror 9 toward the concave mirror 5. Since both the mirror 9 and the mirror 21 are planar mirrors, the beam will run parallel between these two mirrors, so that the variation of the distance will have no effect on the beam. The displacement of the focal point 14 is produced only by varying the distance between mirrors 5 and 6. In another embodiment, which is not represented, the curvatures of the mirrors 5 and 6 can be reversed. The beam 25 is therefore expanded, which results in a focal point 14 at a smaller distance from the mirror 6 which can be refracted according to Gaussian optical formulas.

Figure 3:
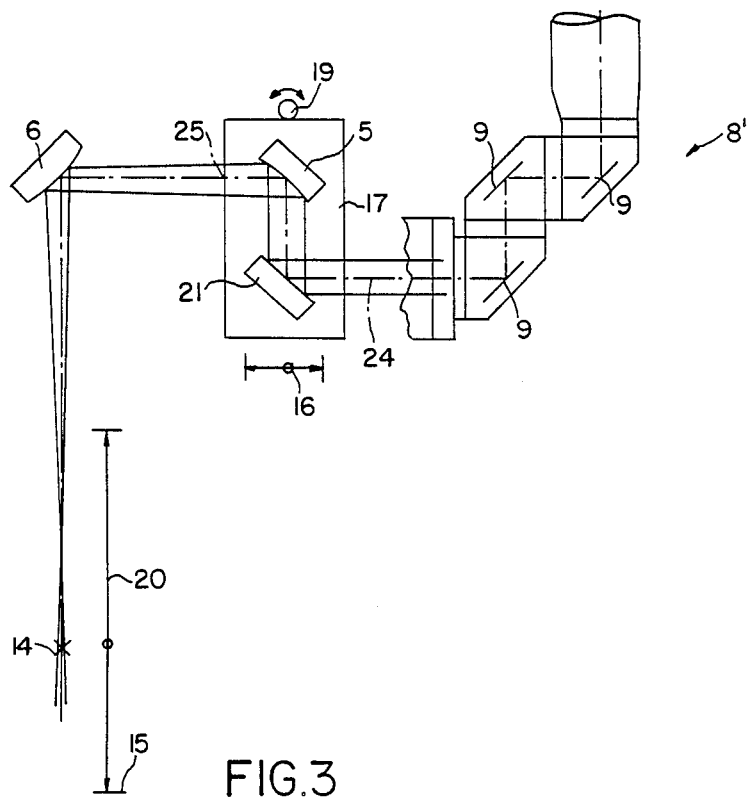
FIG. 3 shows diagrammatically a system in which, in contrast to the embodiment of FIG. 2, the displaceable carriage and one deflecting mirror are mechanically uncoupled from the beam guiding arm.
Figure 4:
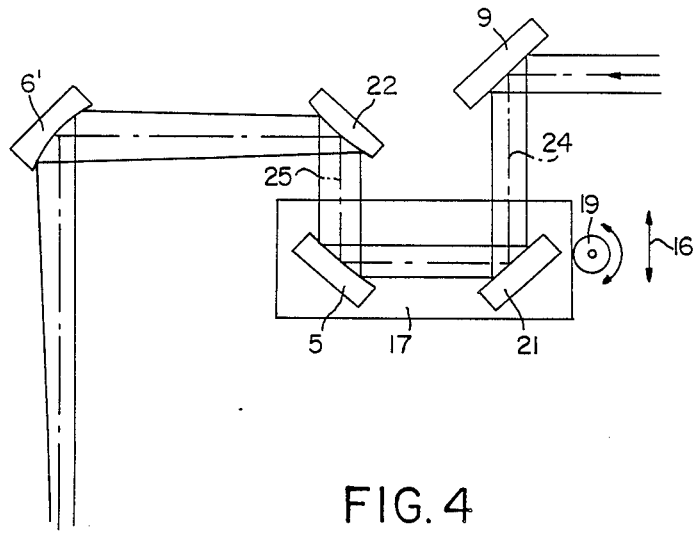
FIG. 4 is a diagrammatic representation of a system in which the adjusting means is displaceable vertically.

In an additional embodiment alternative to FIG. 3, the carriage in the embodiment shown in FIG. 4 is displaceable vertically, and likewise has at the entry end an additional planar mirror 21 plus a concave mirror 5. Outside of the carriage 17, an additional deflecting mirror 22 of convex curvature is provided in addition to the deflecting mirror 6' which has a concave curvature, for the purpose of throwing the beam emerging from carriage 17 through mirror 5 onto the mirror 6' which in this example is concave. In the illustrated embodiment, the convex curvature of the mirror 22 is divided between the two mirrors 5 and 6'. If the curvatures of mirrors 5 and 22 are suitable, the mirror 6' can also be replaced by a planar mirror. The mirror 9, which throws the beam onto the additional planar mirror 21 in the carriage 17, can be the exit mirror of the beam guiding arm 8'.

Figure 5:
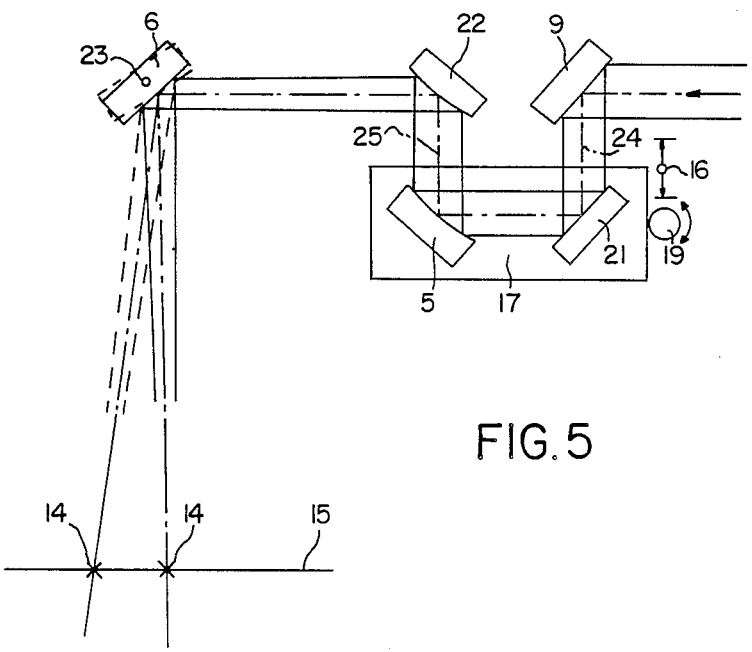
FIG. 5 is a diagrammatic representation of a system in which, in contrast to the embodiment in FIG. 4, a rotatable deflecting mirror is used and the carriage is vertically displaceable.

To be able to move the mirror and the focal point 14 in the working plane, the mirror 6', which in FIG. 5, for example, is a planar mirror, is mounted for rotation about two axes 23 which are perpendicular to one another, and of which only one is shown. In the rest of the arrangement of the mirrors, the embodiment in FIG. 5 is the same as that of FIG. 4.

Figure 6:
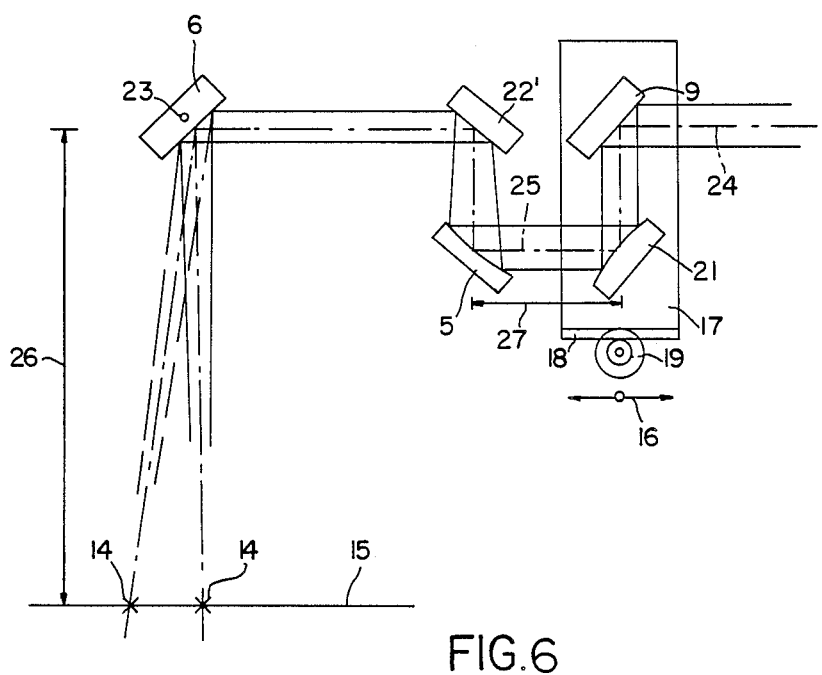
FIG. 6 shows diagrammatically a system similar to FIG. 5, but with a horizontally displaceable carriage.

In the embodiment according to FIG. 6, as in the embodiment in FIG. 5, a planar mirror is used as a rotating mirror on the exit side of the beam system. If a curved mirror is rotated in this case, the laser beam will strike the mirror, not at 45°, but at a variable angle. In the case of angles of incidence other than 45°, the result is an aberration (astigmatism) which intolerably deforms the caustic of the beam in the focusing range. This does not happen with flat mirrors of this kind.

In contrast to the embodiment in FIG. 5, the deflecting mirror 22, marked 22' in FIG. 6, is a planar mirror. Furthermore, the carriage 17 preferably is shifted horizontally, thereby changing the distance between the mirrors 5 and 21. The focal length of the mirror 21

(paraboloid of rotation) according to FIG. 6 preferably amounts to −100 mm, and that of the mirror 5 (ellipsoid of rotation, image scale 1:3) preferably is about 90 mm. The range of displacement 16 of the carriage 17 preferably amounts to 20 mm, the distance between the mirrors 5 and 21, indicated by the arrows 27, preferably is a minimum of 15 mm and a maximum of 35 mm; the focal length, referenced 26 in FIG. 6, preferably is accordingly a minimum of 250 mm and a maximum of 400 mm.

As can be seen in the Figs. the axes of displacement of the carriage 17, which are indicated by the arrows 16, are parallel to the beam axes of the entry beam 24 striking the entry mirror of the carriage, and of the exit beam 25. Basically, the displacement of the carriage 17 varies the distance between a convex and a concave mirror, so that the focal plane changes with the change in the distance. The two mirrors of complementary curvature, which are surface elements of solids of rotation of cone segments, i.e., ellipsoid-of-rotation or paraboloid-of-rotation surface elements, are so aligned with one another that the corresponding focal points of the deflecting mirror in the path outside the adjusting means are in a plane which is spanned by the incident and the reflected beams of that deflecting mirror.

While there have been described what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. A beam guiding optical system for laser radiation, especially for the radiation of a medical laser, for the stepless variation of the focal length, comprising:

adjusting means acting on parts of the beam guiding optical system, said adjusting means comprising a linearly movable carriage which bears at least two carriage mirrors disposed with respect to one another, at least one of these carriage mirrors being concavely or convexly curved;

an entry beam falling on a mirror having a beam axis which is parallel to a beam axis of a beam emerging from said adjusting means, and said carriage having an axis of displacement being aligned parallel to the beam axis of the entry and emerging beams;

at least one deflecting mirror being disposed in a beam path outside of said adjusting means, which has a carriage mirror of a curvature complementary to the curvature of said at least one curved carriage mirror, the mirrors of complementary curvature, which are surface elements of solids of rotation of conic sections, being aligned with one another such that the corresponding focal points of the at least one deflecting mirror in the beam path outside said adjusting means lie in the plane which is spanned by the incident and reflected beam of said at least one deflecting mirror.

2. A beam guiding optical system according to claim 1, in which said at least two carriage mirrors are fixedly disposed with respect to one another.

3. A beam guiding optical system according to claim 1, in which one of said carriage mirrors is the last carriage mirror reflecting the emerging beam and seen in the beam direction, is the concave or convexly curved mirror.

4. A beam guiding optical system according to claim 3, in which another of said carriage mirrors is the first carriage mirror reflecting the entry beam and seen in the beam direction, is a planar mirror.

5. A beam guiding optical system according to claim 3, in which said one of said carriage mirrors is a convexly curved mirror.

6. A beam guiding optical system according to claim 1, which said at least one deflecting mirror seen in the beam direction, is disposed after the adjusting system.

7. A beam guiding optical system according to claim 6, in which said at least one deflecting mirror is disposed for rotation about at least one axis perpendicular to the plane of the emerging beam.

8. A beam guiding optical system according to claim 1, in which said carriage and said at least one deflecting mirror form one structural unit.

9. A beam guiding optical system according to claim 8, which includes a beam guiding arm having a plurality of joints and in which said structural unit includes said carriage and said at least one deflecting mirror is disposed on said beam guiding arm.

10. A beam guiding optical system according to claim 1, which includes a gear drive and in which said carriage is linearly displaceable by means of said gear drive.

11. A beam guiding optical system according to claim 10, in which said carriage is guided in the direction of adjustment and has a rack and in which said gear drive comprises a pinion engaged with said rack.

* * * * *